United States Patent [19]

Tse

[11] Patent Number: 5,090,568
[45] Date of Patent: Feb. 25, 1992

[54] GLASS SLIDE MAILER

[75] Inventor: Tenny P. Tse, Cooper City, Fla.

[73] Assignee: Medscand (U.S.A.), Inc., Hollywood, Fla.

[21] Appl. No.: 667,212

[22] Filed: Mar. 11, 1991

[51] Int. Cl.$^5$ ............................................. B65D 85/48
[52] U.S. Cl. ............................................. 206/456
[58] Field of Search ................................ 206/454, 456

[56] References Cited

U.S. PATENT DOCUMENTS

| | | | |
|---|---|---|---|
| 3,710,975 | 1/1973 | Jansen | 206/456 X |
| 3,756,393 | 9/1973 | Markwitz et al. | 206/456 |
| 4,077,515 | 3/1978 | Shoberg | 206/456 |
| 4,078,656 | 3/1978 | Crane et al. | 206/223 |
| 4,589,551 | 5/1986 | Hellon | 206/456 |
| 4,819,804 | 4/1989 | Levy | 206/456 |

OTHER PUBLICATIONS

Photocopy reproduction and photographs of seven glass slide mailers on sale or public use prior to 3/11/91.

Primary Examiner—William I. Price
Attorney, Agent, or Firm—Roylance, Abrams, Berdo & Goodman

[57] ABSTRACT

A glass slide mailer formed of one piece of molded, resilient polymeric material and comprising a base, a cover, and a living hinge section, the base and cover being pivoted about the hinge section and snap-fitted together at two areas to retain the slide therein. The base has a rectangular cavity for receiving the slide defined by first and second end walls, a pair of side walls, and a bottom wall, and the cover has a first protrusion frictionally engageable with the first end wall and the two side walls of the base and a second protrusion frictionally engageable with the second end wall and the two side walls of the base to snap-fit the cover to the base to retain the slide therein. In the closed position, the first protrusion engages the glass slide to resist relative movement thereof. The side walls have notches for ease of applying a tissue sample to the slide mounted in the mailer. The cover and base have reinforcing transverse and longitudinal ribs, as well as peripheral lips to aid in opening the mailer.

22 Claims, 2 Drawing Sheets

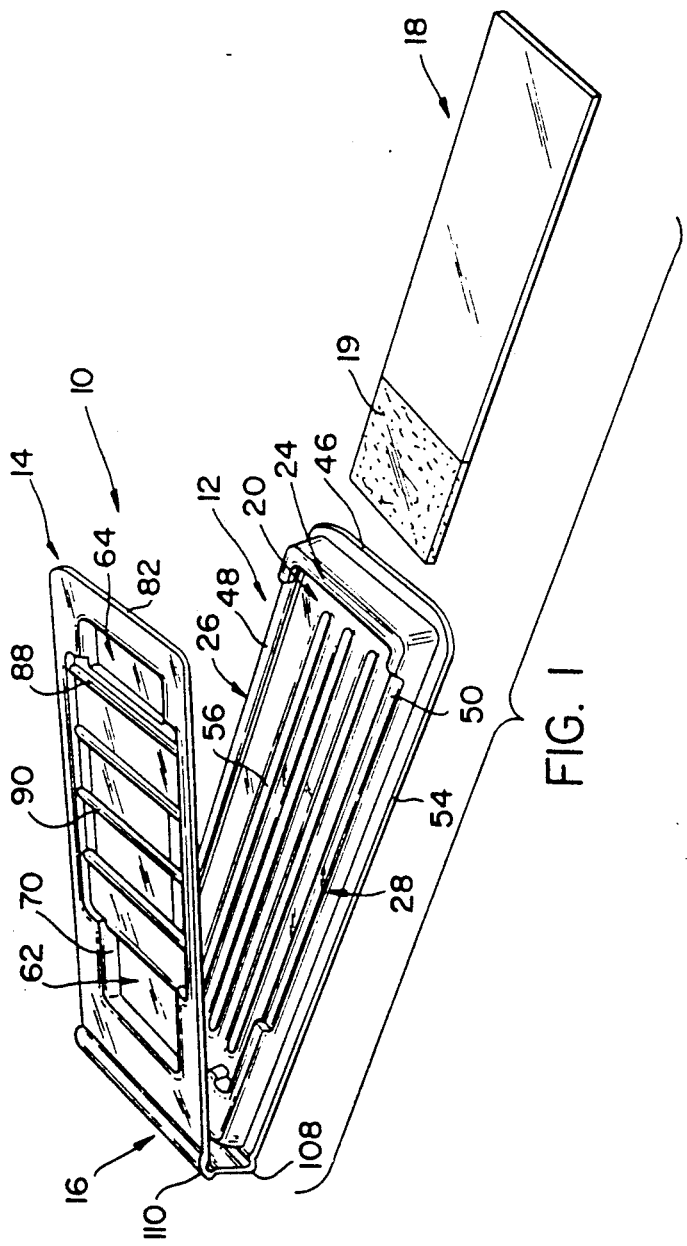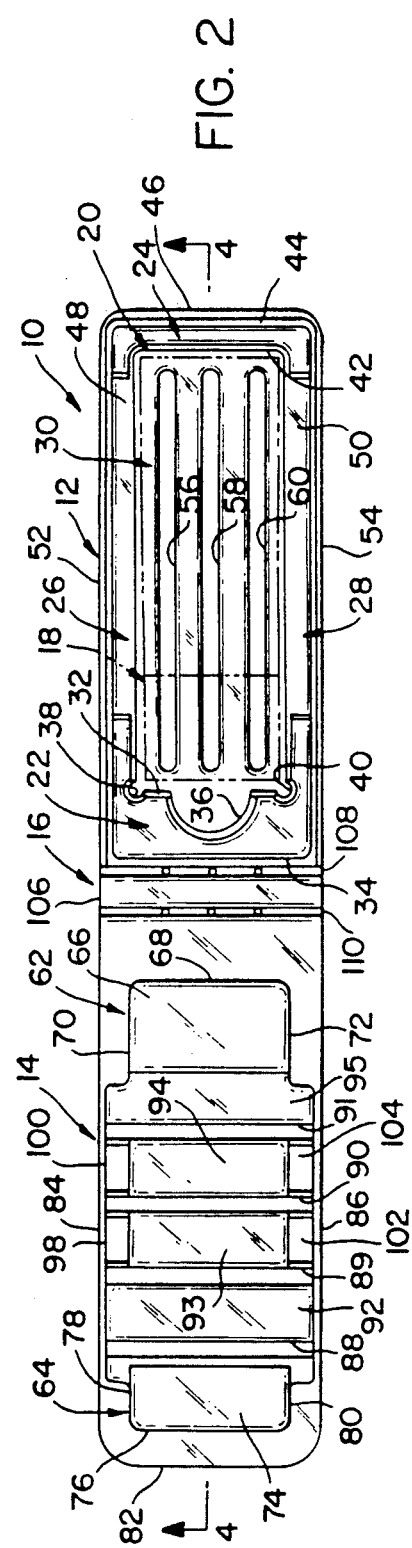

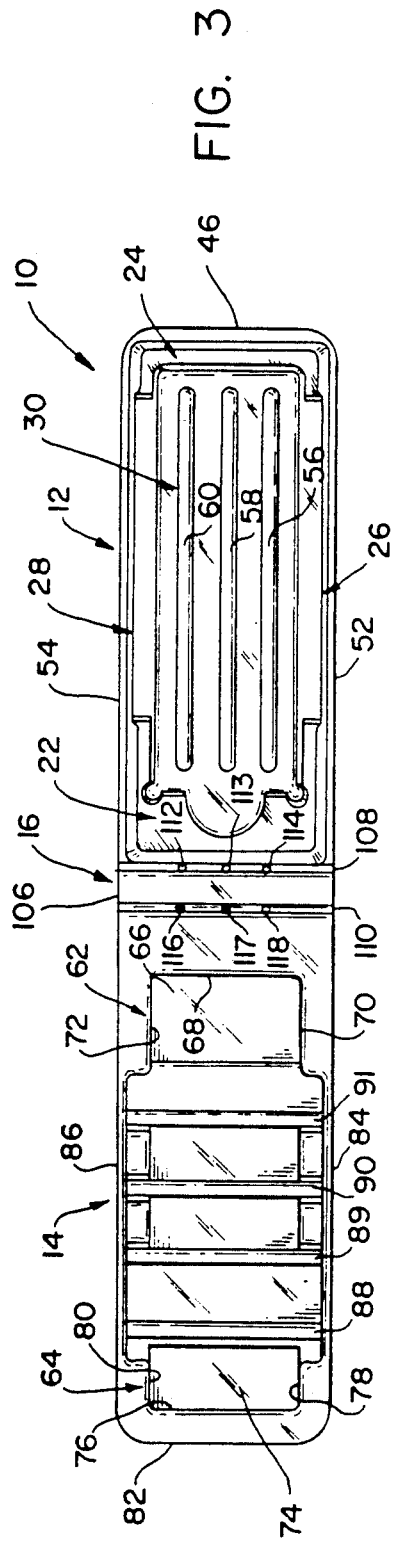

GLASS SLIDE MAILER

FIELD OF THE INVENTION

The invention relates to devices for enclosing and protecting glass slides which bear tissue samples and which are being transmitted to a laboratory for testing. More specifically, the invention relates to a glass slide mailer formed of one piece of molded, resilient polymeric material and comprising a base, a cover, and a hinge section, the base and cover being pivoted about the hinge section and snap-fitted together to retain the slide therein.

BACKGROUND OF THE INVENTION

Glass slides are used extensively in laboratories to mount tissue samples for testing, for example, for possible pathology. In practice, once the tissue sample is taken from the patient, it is then smeared onto the slide and fixed with a fixative. Then, the slide bearing the tissue sample is transmitted to a laboratory where various tests can be performed on the sample. To assure receipt of the glass slide and tissue sample at the laboratory in good condition, the glass slide is typically enclosed in some type of protective device.

While there have been numerous devices in the past utilized for transporting glass slides, they have numerous disadvantages and drawbacks. For example, many of them are extremely difficult to use since they are difficult to open and close and cumbersome to insert and remove a slide. In addition, many of these devices cannot support a slide therein for unobstructed application of the tissue sample, thereby losing some of the sample. Many of these devices also are prone to breaking and do not provide secure enclosure for the glass slide. Moreover, many of these devices are relatively expensive and difficult to manufacture and do not adequately protect the slide from breaking and the tissue sample from smearing during transit.

An example of one of these prior devices is disclosed in U.S. Pat. No. 4,078,656 to Crane et al.

SUMMARY OF THE INVENTION

Accordingly, a primary object of the present invention is to provide a glass slide mailer which is relatively simple to use and can be easily opened and closed.

Another object of the invention is to provide a glass slide mailer which can easily receive and release a slide therefrom and can provide unobstructed smearing of a tissue sample on the glass slide while received therein.

Another object of the invention is to provide a glass slide mailer that is durable and can be easily and securely closed.

A further object of the invention is to provide a glass slide mailer that is relatively inexpensive and easy to manufacture and can protect the glass slide from breaking and the tissue sample thereon from smearing during transit.

The foregoing objects are basically attained by providing a glass slide mailer, the combination comprising a base having a glass slide receiving cavity defined by a first end wall, a second end wall, a pair of side walls, and a bottom wall, the first and second end walls each having an inner surface facing the cavity; a cover having a first protrusion extending therefrom and frictionally engageable with the inner surface on the first end wall of the base, and a second protrusion extending therefrom and frictionally engageable with the inner surface on the second end wall of the base, the first protrusion having a portion engageable with the glass slide; and a hinge section having a first hinge pivotally interconnecting the hinge section and the base, and a second hinge pivotally interconnecting the hinge section and the cover.

Other objects, advantages and salient features of the invention will become apparent from the following detailed description, which, taken in conjunction with the annexed drawings, discloses a preferred embodiment of the invention.

BRIEF DESCRIPTION OF THE DRAWINGS

Referring to the drawings which form a part of this original disclosure:

FIG. 1 is a left perspective view of the glass slide mailer in accordance with the invention in its open position with a glass slide located adjacent thereto;

FIG. 2 is a top plan view of the inside of the glass slide mailer shown in FIG. 1 in its fully open position;

FIG. 3 is a bottom plan view of the outside of the glass slide mailer shown in FIG. 2;

FIG. 4 is an enlarged side elevational view in substantially longitudinal section taken along line 4—4 in FIG. 2 of the glass slide mailer in accordance with the present invention in its fully open position with a glass slide being located above the base; and FIG. 5 is a side elevational view in longitudinal section of the glass slide mailer as shown in FIG. 4, except that the slide has been received in the base and the cover has been pivoted into its closed position snap-fitted to the base, an adhesive label about to be connected to the end of the closed mailer.

DETAILED DESCRIPTION OF THE INVENTION

Referring now to FIGS. 1-5, the glass slide mailer 10 in accordance with the invention is shown as being formed integrally of a one-piece molded, resilient and preferably transparent polymeric material and comprises a base 12, a cover 14, and a hinge section 16. In the open positions shown in FIGS. 1-4, a glass slide 18 can be placed in the base 12 and then the cover 14 can be pivoted relative thereto along the hinge section 16 to a closed position shown in FIG. 5 in which the base and cover are snap-fitted together in two areas.

The glass slide mailer 10 is preferably about four inches long and about 5/16 inch thick when folded, and about one and one-half inches wide, and is formed of a material about 1/64 inch thick substantially uniformly throughout. Preferably, the material is 20 gauge, clear polyvinylchloride. Since it is transparent, a technician can easily tell if a slide is in fact in the mailer before opening it and can easily determine if the slide is broken. The glass slide 18 is rectangular, about 3/64 inch thick, about three inches long and about one inch wide.

Base 12 has a rectangular, upwardly opening cavity 20 defined therein by four substantially planar upstanding walls comprising a first end wall 22, a second end wall 24, and first and second side walls 26 and 28, and by a substantially planar bottom wall 30. These walls are hollow and have substantially U-shaped transverse cross sections, as seen in FIGS. 3 and 4. The rectangular cavity 20 is slightly larger than the glass slide 18, as seen in FIG. 2.

The first end wall 22 has an inner surface 32 facing towards the cavity 20 and an outer surface 34 which is overlaid by the hinge section 16 after the cover and base are pivoted towards each other as illustrated in FIG. 5. Formed in inner surface 32 on the first end wall 22 is a first or central recess 36 which is semicircular and faces the cavity and which allows for insertion of the technician's fingertip therein to aid in removing the glass slide from the base. On opposite sides of the first recess 36 are second and third recesses 38 and 40 formed in the inner surface 32 which likewise aid in removing the slide from the base, especially if the bottom of the slide is wet.

The second end wall 24 also has an inner surface 42 facing towards the cavity 20 and an outer surface 44 facing away from the cavity. Extending outwardly from the bottom of outer surface 44 and substantially parallel to bottom wall 30 is a first substantially planar lip 46 which spans the width of the base and which aids in opening of the mailer by providing a convenient place for the technician's fingertip.

The first side wall 26 has an elongated notch 48 with a substantially planar bottom surface extending a significant portion of its length, the notch having a depth sufficiently deep so that the top of the slide is substantially coplanar with the bottom surface of the notch to allow for substantially unobstructed access and ease of smearing of the slide with the tissue sample when the slide is received in the base. Thus, the height of the side wall along the notch from the bottom wall is substantially equal to the thickness of the glass slide. The second side wall 28 has a similar notch 50 therein. Each of the notches has a length at least equal to about one-half the length of the slide, and preferably substantially equal to the length of the slide between the edge of the frosted end 19 and the opposite clear end of the slide. In the preferred embodiment, these lengths are both equal to about 2 ¼ inch.

Extending outwardly past the first side wall 26 and substantially parallel to bottom wall 30 is a substantially planar side lip 52 which extends from the hinge section 16 to the first lip 46 at the second end wall of the base. A similar side lip 54 is formed on the second side wall 28.

The planar bottom wall 30 is reinforced via three longitudinally extending parallel ribs 56, 58 and 60 which extend downwardly from the surface of the bottom wall, have a substantially curved cross section, and extend almost completely between the first and second end walls 22 and 24 of the base. These ribs aid in resisting unwanted bending of the base about an axis transverse to the longitudinal axis thereof.

As seen in FIGS. 2-5, the cover 14 has first and second substantially rectangular parallelopiped protrusions 62 and 64 which will snap-fit frictionally with the base to close the cover against the base with the glass slide 18 therein as seen in FIG. 5. The first protrusion 62 is adjacent the hinge section 16 and has a substantially planar bottom surface or portion 66 which extends outwardly from the cover a sufficient depth so that it engages the glass slide 18, as seen in FIG. 5, when the cover and base are snapped together. Advantageously, the bottom surface 66 engages the frosted end 19 on the glass slide which does not contain any tissue sample which could otherwise be smeared or adversely affected. This engagement also aids in preventing movement of the slide relative to the mailer which would otherwise increase the possibility of chipping or breaking the slide or smearing the tissue sample. The first protrusion 62 also has a first end surface 68 substantially perpendicular to bottom surface 66 which frictionally engages in an interference fit with the first end wall inner surface 32 on the base as seen in FIG. 5. The first protrusion 62 also has a pair of opposed side portions or surfaces 70 and 72 extending substantially perpendicular to bottom surface 66 which frictionally engage in an interference fit with corresponding inner surfaces on the first and second side walls 26 and 28 of the base adjacent the first end wall 22 of the base.

The second protrusion 64 is near the distal end of the cover and has a similar planar bottom surface 74, and an end surface 76 and two side surfaces or portions 78 and 80 extending substantially perpendicular to the bottom surface 74. The bottom surface 74 of the second protrusion is closer to the outer surface of the cover than bottom surface 66 on the first protrusion and thus does not extend as deeply into the base as does bottom surface 66 on the first protrusion so as not to smear the tissue sample on the glass slide as seen in FIG. 5. The end surface 76 frictionally engages in an interference fit with inner surface 42 on the second end wall of the base and the side surfaces 78 and 80 frictionally engage in an interference fit with the inner surfaces of the side walls 26 and 28 of the base adjacent the second end wall as illustrated in FIG. 5 to aid in securely snap-fitting the cover to the base.

Extending outwardly from end surface 76 on the cover is a second substantially planar lip 82 which engages the top of the second end wall 24 of the base when the cover is fully pivoted and snap-fitted onto the base as seen in FIG. 5. In this closed position, the first lip 46 on the base and the second lip 82 on the cover are substantially parallel and spaced apart a significant distance, at least equal to the thickness of the glass slide, so that the technician can easily grasp both lips and pull the cover and base away from one another to gain access to the slide inside. Although not shown, lip 82 can be enlarged by about 3/16 inch so that it clearly extends past lip 46 in the closed position.

The cover 14 also has a pair of substantially planar side lips 84 and 86, which extend outwardly, respectively, past the side walls 26 and 28 of the base when the cover is snap-fitted to the base. Thus, these side lips 84 and 86 can be grasped in addition to the side lips 52 and 54 on the base to once again aid in opening the glass slide mailer 10 by pivoting the cover and base away from one another. Advantageously, the side lips 84 and 86 on the cover and the side lips 52 and 54 on the base are substantially parallel and spaced apart a significant amount, at least equal to the thickness of the glass slide, to allow for the technician's fingers to be able to grasp the various lips easily when the mailer is in the closed position.

The cover 14 also has four spaced apart and parallel transverse ribs 88-91 which have a substantially curved configuration in cross section and an additional four spaced apart and parallel transverse ribs 92-95 which have a substantially U-shaped cross section and are wider than ribs 88-91. As seen in FIGS. 2-5, ribs 88-91 and 92-95 are alternately provided on the cover between the first and second protrusions 62 and 64. These ribs aid in resisting bending of the cover about its longitudinal axis, and when coupled with the base in the closed position, also resist bending of the entire mailer 10 around that longitudinal axis.

As seen in FIGS. 2-5, a pair of side protrusions or teeth 98 and 100 extend outwardly of the cover from ribs 93 and 94 at one side of the cover, and similarly a second pair of side protrusions or teeth 102 and 104 extend outwardly from ribs 93 and 94 on the other side of the cover. These protrusions engage the bottom surfaces of notches 48 and 50 in the side walls of the base as seen in FIG. 5 once the cover is fully engaged with the base and aid in resisting crushing of the cover against the slide, allowing trapped air to escape from the inside of the mailer during closing to facilitate easy closing, and preventing the cover from touching the patient's specimen smeared on the slide.

The hinge section 16 comprises a central planar rectangular member 106 with a first hinge 108 on one edge pivotally interconnecting the hinge section with the base, and a second hinge 110 on the opposite edge pivotally interconnecting the hinge section to the cover.

Each of the first and second hinges 108 and 110 are substantially U-shaped, elongated members formed integrally as living hinges between the rectangular member 106 and the base and cover. Three spaced perforations 112, 113 and 114 are formed through the first hinge 108 and three spaced perforations 116-118 are formed through the second hinge 110 as seen in FIG. 3. These perforations are optional and, if used, aid in preventing the rectangular member 116 from bending and resisting the cover from moving away from the base in the closed position.

In this closed position, the rectangular member 106 of the hinge section overlies the outer surface 34 on the first end wall 22 of the base.

In the closed position shown in FIG. 5, an adhesive label 120 can be applied to the engaging ends of the cover and base of the mailer to more securely close the mailer, provide a security seal which would be tamper evident, and to provide a space for various indicia to be noted on the mailer, such as the patient's name. Alternatively, the label can be applied transversely across the center of the cover and base and wrapped with a rubber band.

Preferably, the distance between inner surface 32 on the first end wall 22 of the base and inner surface 42 on the second end wall 24 of the base is slightly smaller than the distance between end surface 68 on the first protrusion 62 and end surface 76 on the second protrusion 64. This not only provides the respective interference fits therebetween, but also results in the cover 14 bowing outwardly slightly in the closed position. Since the cover is formed of resilient material, this bowed configuration provides a compressive force tending to keep the protrusions against the respective inner surfaces and thus more securely snap-fits the cover to the base.

While a particular embodiment has been chosen to illustrate the invention, it will be understood by those skilled in the art that various changes and modifications can be made therein without departing from the scope of the invention as defined in the appended claims. For example, notch 48 in side wall 26 on the base can be eliminated, and so can teeth 98 and 100 on the cover. In addition, ribs 88-91 and 92-95 on the cover can be shortened in length so that side lip 84 becomes wider in the area between protrusions 62 and 64, in effect being as wide as it is between its distal edge and the sides of protrusions 62 and 64. The effect of this would be to strengthen the mailer against bending about its transverse axis, since side wall 26 would be deeper along its entire length.

What is claimed is:

1. A glass slide mailer, the combination comprising:

a base having a glass slide receiving cavity define by a first end wall, a second end wall, a pair of side walls, and a bottom wall, said first and second end walls each having an inner surface facing said cavity;

a cover having a first protrusion extending therefrom and frictionally engageable with said inner surface on said first end wall of said base, and a second protrusion extending therefrom and frictionally engageable with said inner surface on said second end wall of said base, said first protrusion having a portion engageable with the glass slide; and a hinge section having a first hinge pivotally interconnecting said hinge section and said base, and a second hinge pivotally interconnecting said hinge section and said cover.

2. A glass slide mailer according to claim 1, wherein said base, cover and hinge section are integrally formed of one piece of resilient polymeric material.

3. A glass slide mailer according to claim 1, wherein said bottom wall has a plurality of longitudinally extending ribs.

4. A glass slide mailer according to claim 1, wherein at least one of said side walls has a notch therein.

5. A glass slide mailer according to claim 1, wherein said cavity is substantially rectangular.

6. A glass slide mailer according to claim 1, wherein said first end wall has a first recess therein.

7. A glass slide mailer according to claim 6, wherein said first end wall has second and third recesses therein on opposite sides of said first recess.

8. A glass slide mailer according to claim 1, wherein said first protrusion portion engageable with the glass slide is substantially planar.

9. A glass slide mailer according to claim 1, wherein said first protrusion has a pair of side portions each of which is frictionally engageable with one of said pair of side walls, said second protrusion has a pair of side portions, each of which is frictionally engageable with one of said pair of side walls.

10. A glass slide mailer according to claim 1, wherein said cover has a plurality of transversely extending ribs.

11. A glass slide mailer according to claim 1, wherein said cover has a pair of side protrusions on opposite sides thereof engageable with said base.

12. A glass slide mailer according to claim 1, wherein said hinge section comprises a substantially planar rectangular member, said first hinge comprises a substantially U-shaped member, and said second hinge comprises a substantially U-shaped member.

13. A glass slide mailer according to claim 1, wherein said first hinge has at least one perforation therein, and said second hinge has at least one perforation therein.

14. A glass slide mailer according to claim 1, wherein said base has a first lip extending past said second end wall, and said cover has a second lip extending past said second end wall when said cover and base are frictionally engaged, said first and second lips being spaced apart in such engaged position by at least the thickness of the glass slide.

15. A glass slide mailer according to claim 14, wherein
    said base has a pair of side lips, each of which extends past one of said pair of side walls, and
    said cover has a pair of side lips, each of which extends past one of said pair of side walls when said cover and base are frictionally engaged,
    said pair of side lips on said base and said pair of side lips on said cover being spaced apart in such engaged position by at least the thickness of the glass slide.

16. A glass slide mailer, the combination comprising:
    a base having a glass slide receiving cavity defined by a first end wall, a second end wall, a pair of side walls, and a bottom wall, said first and second end walls each having an inner surface facing said cavity;
    a cover having a first protrusion extending therefrom and frictionally engageable with said inner surface on said first end wall of said base, and a second protrusion extending therefrom and frictionally engageable with said inner surface on said second end wall of said base; and
    a hinge section pivotally interconnecting said base and said cover,
    at least one of said side walls in said base having a notch therein.

17. A glass slide mailer according to claim 16, wherein
    said notch has a substantially planar bottom surface substantially coplanar with the top surface of the glass slide.

18. A glass slide mailer according to claim 16, wherein
    a side protrusion on one side thereof which is engageable with the bottom surface of said notch when said cover and base are frictionally engaged.

19. A glass slide mailer according to claim 16, wherein
    said notch has a length at least equal to about one-half the length of the slide.

20. A glass slide mailer, the combination comprising:
    a base having a glass slide receiving cavity defined by a first end wall, a second end wall, a pair of side walls, and a bottom wall, said first and second end walls each having an inner surface facing said cavity;
    a cover having a first protrusion extending therefrom and frictionally engageable with said inner surface on said first end wall of said base, and a second protrusion extending therefrom and frictionally engageable with said inner surface on said second end wall of said base; and
    a hinge section pivotally interconnecting said base and said cover,
    said base having a first lip extending past said second end wall, and
    said cover having a second lip extending past said second end wall when said cover and base are frictionally engaged,
    said first and second lips being spaced apart in such engaged position by at least the thickness of the glass slide.

21. A glass slide mailer according to claim 20, wherein
    said base has a pair of side lips, each of which extends past one of said pair of side walls, and
    said cover has a pair of side lips, each of which extends past one of said pair of side walls when said cover and base are frictionally engaged,
    said pair of side lips on said base and said pair of side lips on said cover being spaced apart in such engaged position by at least the thickness of the glass slide.

22. A glass slide mailer according to claim 20, wherein
    said base, cover and hinge section are integrally formed of one piece of resilient polymeric material having a substantially uniform thickness.

* * * * *

UNITED STATES PATENT AND TRADEMARK OFFICE
CERTIFICATE OF CORRECTION

PATENT NO. : 5,090,568

DATED : February 25, 1992

INVENTOR(S) : Tenny P. Tse

It is certified that error appears in the above-identified patent and that said Letters Patent is hereby corrected as shown below:

Column 6, line 1, "define" should read -- defined --.

Column 6, line 37, after "side portions" should appear -- , --.

Column 7, line 37, before "a side protrusion" should appear -- said cover has --.

Signed and Sealed this

Twenty-first Day of September, 1993

Attest:

BRUCE LEHMAN

Attesting Officer

Commissioner of Patents and Trademarks